(12) United States Patent
Gibbins

(10) Patent No.: US 6,355,858 B1
(45) Date of Patent: Mar. 12, 2002

(54) WOUND DRESSING DEVICE

(75) Inventor: Bruce L. Gibbins, Lake Oswego, OR (US)

(73) Assignee: AcryMed, Inc., Portland, OR (US)

( * ) Notice: Subject to any disclaimer, the term of this patent is extended or adjusted under 35 U.S.C. 154(b) by 0 days.

(21) Appl. No.: 09/191,223

(22) Filed: Nov. 13, 1998

Related U.S. Application Data

(63) Continuation-in-part of application No. 08/971,074, filed on Nov. 14, 1997, now Pat. No. 5,928,174.

(51) Int. Cl.$^7$ ................................................ A61F 13/00
(52) U.S. Cl. ........................................................ 602/41
(58) Field of Search .............................. 602/43, 41, 48

(56) References Cited

U.S. PATENT DOCUMENTS

| | | | |
|---|---|---|---|
| 3,157,524 A | 11/1964 | Artandi | 106/122 |
| 3,645,835 A | 2/1972 | Hodgson | 161/146 |
| 3,969,498 A | 7/1976 | Catania et al. | 424/28 |
| 4,306,551 A | 12/1981 | Hymes et al. | 128/156 |
| 4,320,201 A | 3/1982 | Berg et al. | 435/265 |
| 5,196,190 A | 3/1993 | Nangia et al. | 424/78.06 |
| 5,660,854 A | * 8/1997 | Haynes et al. | |

FOREIGN PATENT DOCUMENTS

| | | |
|---|---|---|
| EP | 0 072 251 | 2/1983 |
| EP | 0 297 769 | 1/1989 |
| EP | 0 489 206 | 6/1992 |
| EP | 0 709 101 | 5/1996 |
| GB | 1471013 | 4/1977 |
| GB | 1 554 002 | 10/1979 |
| JP | 6-145060 | 5/1994 |
| WO | WO 88/06894 | 9/1988 |
| WO | WO 90/03810 | 4/1990 |

* cited by examiner

Primary Examiner—Michael A. Brown
Assistant Examiner—Lalita M. Hamilton
(74) Attorney, Agent, or Firm—Kilpatrick Stockton LLP

(57) ABSTRACT

The present invention comprises methods and compositions for treating wounds. More particularly, the present invention comprises methods and compositions for wound dressing devices comprising a matrix comprising a polymer network and a non-gellable polysaccharide having active agents, such as wound healing agents, incorporated therein. The matrix may be formed into any desired shape for treatment of wounds.

16 Claims, 3 Drawing Sheets

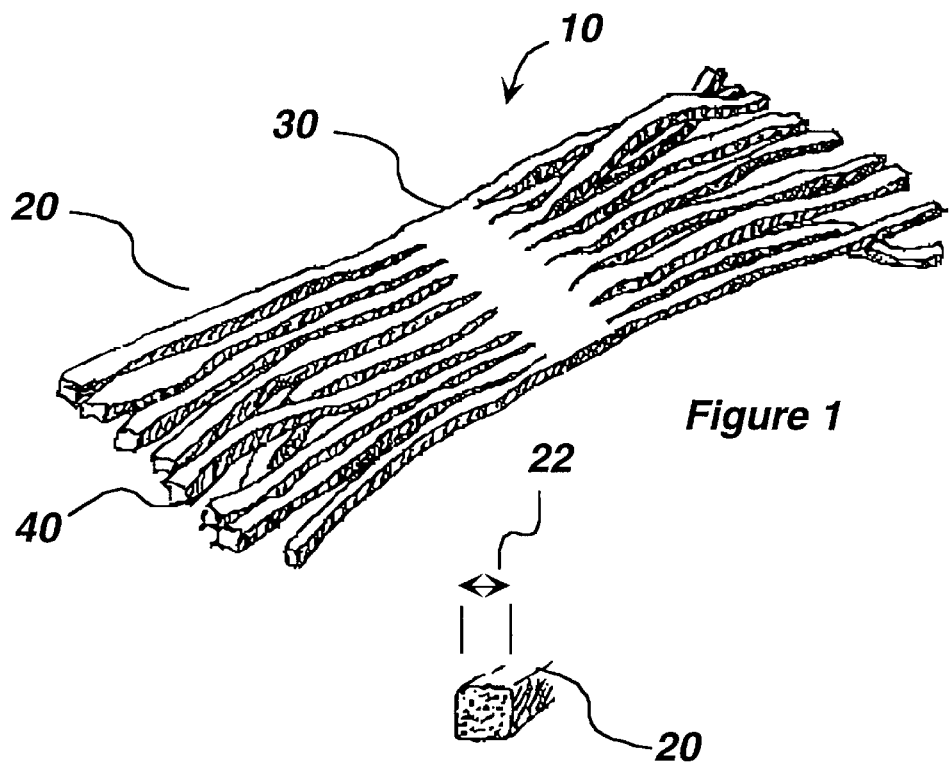
*Figure 1*
*Figure 2*
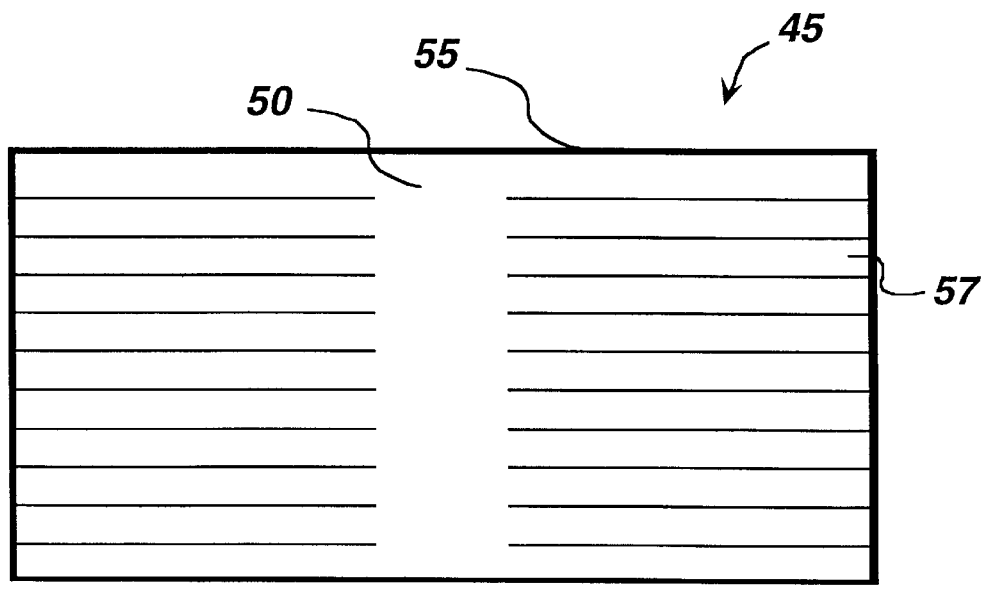
*Figure 3*

WOUND DRESSING DEVICE

CROSS-REFERENCE TO RELATED APPLICATIONS

This application is a continuation-in-part of U.S. patent application Ser. No. 08/971,074, filed Nov. 14, 1997, now U.S. Pat. No. 5,928,174.

FIELD OF THE INVENTION

The present invention relates generally to the field of wound dressings and particularly to compositions and methods for delivering active agents to wounds. More particularly, the present invention relates to treatments of wounds in providing methods and compositions for debridement of wounds and delivery of wound healing compositions.

BACKGROUND OF THE INVENTION

The outer layer of skin surrounding the body performs an important protective function as a barrier against infection, and serves as a means of regulating the exchange of heat, fluid and gas between the body and external environment. When skin is removed or damaged by being abraded, burned or lacerated, this protective function is diminished. Areas of damaged skin are conventionally protected by the application of a wound dressing which facilitates wound healing by acting as a skin substitute.

Wounds to skin and the underlying tissues of animals may be caused by external insult such as friction, abrasion, laceration, burning or chemical irritation. Damage to such tissues may also result from internal metabolic or physical dysfunction, including but not limited to bone protrudence, diabetes, circulatory insufficiencies, or inflammatory processes. Normally tissue damage initiates physiological processes of regeneration and repair. In broad terms, this process is referred to as the wound healing process.

The wound healing process usually progresses through distinct stages leading to the eventual closure, and restoration of the natural function of the tissues. Injury to the skin initiates an immediate vascular response characterized by a transient period of vasoconstriction, followed by a more prolonged period of vasodilation. Blood components infiltrate the wound site, endothelial cells are released, exposing fibrillar collagen, and platelets attach to exposed sites. As platelets become activated, components are released which initiate events of the intrinsic coagulation pathway. At the same time, a complex series of events trigger the inflammatory pathways generating soluble mediators to direct subsequent stages of the healing process.

Normally, the wound healing process is uneventful and may occur regardless of any intervention, even in the case of acute or traumatic wounds. However, where an underlying metabolic condition or perpetual insult such as pressure is a contributing factor, the natural wound healing process may be retarded or completely arrested, resulting in a chronic wound. Trends in modern medical practices have shown that the wound healing of both acute and chronic wounds may be significantly improved by clinical intervention using methods and materials that optimize wound conditions to support the physiological processes of the progressive stages of wound healing. Key factors in providing the optimal conditions are the prevention of scab formation and the maintenance of an optimal level of moisture in the wound bed. Both of these factors can be controlled by the management of wound exudate fluid.

A common problem in the management of both acute and chronic wounds is the maintenance of an optimal level of moisture over the wound bed during heavy exudate drainage. This is usually, but not always, an early stage of healing. Most moist wound dressing technologies such as thin films, hydrocolloid dressings and hydrogels are typically overwhelmed by the accumulated exudate moisture during this heavy drainage phase. Management of moisture during heavy exudate drainage often necessitates the use of gauze or sponge packings that wick away excess moisture from the wound bed, thin film coverings that trap exudate fluid over the wound bed, or calcium alginate dressings that chemically bind exudate moisture due to the hydroscopic properties of the seaweed extract.

Examples of wound dressings that have been developed include collagen dressings. Soluble collagen has been used as a subcutaneous implant for repairing dermatological defects such as acne scars, glabellar furrows, excision scars and other soft tissue defects. Collagen has also been used in many forms as wound dressings such as collagen sponges, as described in Artandi, U.S. Pat. No. 3,157,524 and Berg et al., U.S. Pat. No. 4,320,201. However, most of these dressings are not satisfactory for the various types of full thickness wounds. Collagen films and sponges do not readily conform to varied wound shapes. Furthermore, some collagen wound dressings have poor fluid absorption properties and undesirably enhance the pooling of wound fluids.

Another example of wound dressings that have been developed are hydrocolloid dressings. United Kingdom Patent Number 1,471,013 and Catania et al., U.S. Pat. No. 3,969,498 describe hydrocolloid dressings that are plasma soluble, form an artificial eschar with the moist elements at the wound site, and gradually dissolve to release medicaments. These dressings comprise a hydrophilic foam of dextran polymer that can be applied without therapeutic agents or ointments, are non-irritating to the lesion and can be easily removed.

Known hydrocolloid dressings in general, and the Catania et al. dressings in particular, are subject to a number of drawbacks. The major disadvantages of these dressings include the potential to disintegrate in the presence of excess fluid at the wound site, and minimal, virtually negligible, control over water loss from the wound. This latter disadvantage is particularly important, as excess water loss from a wound will cause an increase in heat loss from the body as a whole, potentially leading to hypermetabolism. In addition, hydrocolloid dressings require frequent dressing changes. This is especially true of the Catania et al. dressing due to the dissolution of the dextran polymer at the wound site caused by the fluid loss through the wound in the exudative stage.

Although currently available dressing materials possess features that contribute to the control of heavy exudate drainage, most also possess significant limitations that retard the overall healing process. For example, thin film dressings such as those described in U.S. Pat. No. 3,645,835, maintain excessive moisture over the wound bed, contributing to the overhydration or maceration of surrounding skin. Although sponges and gauze support tissue, they require frequent changing, and cause irritation to the wound bed during body movement and dressing removal. Calcium alginates turn into a gelatinous mass during interaction with moisture, are difficult to remove completely, and often dehydrate the wound bed due to the hydroscopic nature of the matrix.

Importantly, none of the presently available devices significantly contribute to or support the autolytic debridement phase, which is the natural removal process of necrotic tissue and debris from the wound. Autolytic debridement is a key early stage event that precedes repair phases of healing. When wound conditions are not optimal for supporting autolytic debridement, then clinical procedures such as surgical removal, irrigation, scrubbing, and enzymatic or chemical methods must be used to remove the necrotic tissue and escar that can inhibit wound healing.

Temporary or permanent wound dressings that are designed to enhance wound healing are needed to cover large open wounds on patients with extensive burns, lacerations and skin damage. Furthermore the ability to produce wound dressings in a variety of shapes to accommodate multiple sizes and forms of injuries is important in the manufacture of useful medical products.

In addition, there continues to be a need for a wound dressing that possesses high moisture absorption capacity, a high rate of absorption, as well as a capacity to regulate moisture at the wound bed-dressing interface. Desirably, such a wound dressing device should stimulate the autolytic debridement process, especially during the heavy exudating phase of wound care management.

Another desirable aspect of a wound dressing would be the ability to deliver active agents to the site of injury to accelerate wound healing. Active agents for use in wound treatment may be administered to an individual in a variety of ways. For example, active agents may be administered topically, sublingually, orally, or by injection (subcutaneous, intramuscular or intravenous). Nevertheless, there are drawbacks to many of these methods, and an inexpensive, reliable, localized and relatively pain-free method of administering an active agent has not been provided in the prior art.

One common method employed for the treatment of wounds is the topical application of a salve or ointment. Yet many times, topical application to a wound can be painful. Additionally, in the case of a deeply cavitated wound in particular, an excess of active agent may be required because the agent must diffuse through layers of necrotic tissue and newly forming epidermal tissues. This difficulty in delivering the agent may require the application of an excessive amount of the agent and preclude an accurate determination of the effective amount of active agent to be added.

The oral and sublingual administrations of active agents used in wound treatment also have their drawbacks. Most importantly, the administration site, the mouth, is normally far removed from the actual location of the wound. Ingestion of an active agent at a site distant from the wound may result in the agent having negative system-wide effects and possibly knocking out the normal flora, or normal microbial environment, whose presence benefits an individual. Successful absorption of the agent into the bloodstream also depends on several factors such as the agents stability in gastrointestinal fluids, the pH of the gastrointestinal tract, solubility of solid agents, intestinal motility, and gastric emptying.

Injection of an active agent, a normally painful method of administration, may have the same negative system-wide effects as that of an oral or sublingual administration if injection is at a site distant from the wound. Yet more importantly, a danger inherent in the injection of an active agent is that rapid removal of the agent is impossible once it is administered. There is also a risk of transmission of infections and the possibility of vascular injury due to the use of needles.

Therefore, topical, oral, sublingual and intravenous methods of administration pose several problems when delivering active agents for the treatment of wounds. What is needed is a method of administering an active agent for the treatment of wounds in an effective, safe and relatively pain-free manner.

SUMMARY OF THE INVENTION

The present invention comprises compositions and methods for the treatment of wounds. In particular, the present invention provides methods and compositions for administering active agents to the site of a wound via wound dressings with active agents incorporated therein. The present invention also allows for localized delivery of active agents and prevents the negative effects of system wide administration. The present invention comprises wound healing devices that have specialized structures that aid in treatment of wounds.

In a preferred embodiment of the present invention, active agents are incorporated directly into micro-cavities of the matrix of the wound dressing devices. The agents may be incorporated by absorption of agents by the matrix, and preferably by incorporation during the polymerization of the matrix. It is theorized that the release of the active agents may be controlled via manipulation of concentration parameters, movement of water through the matrix and the degree of cross linking in the matrix. In a further preferred embodiment, the wound dressings comprise a stranded configuration, wherein the strands extend from at least one common region and the strands themselves comprise a polymer matrix.

The wound dressing devices of the present invention may be used to simultaneously deliver a number of active agents to a wound site. Wound healing agents such as antimicrobial agents, antifungal agents, antiviral agents, growth factors, angiogenic factors, anaesthetics, mucopolysaccharides and other wound healing proteins may be incorporated into the wound dressings for controlled release. Adjuvants and other agents, such as those that boost the immune system, may also be incorporated into the wound dressings devices of the present invention. A surprising and novel aspect of the preferred embodiment having agents directly incorporated into micro-cavities of the matrix is that the activities of the wound healing agents are not altered by incorporation into the devices and that the agents are effective upon their release.

In a preferred embodiment of the present invention, the wound dressing devices of the present invention comprise a novel stranded structure made from a matrix suitable for application to broken skin and underlying tissues. The individual strands of the preferred embodiment may or may not have free floating ends, however, the unique arrangement of the device allows it to both absorb excess wound exudate, and simultaneously conform closely to the walls of the wound bed, in order to accelerate overall wound healing.

The preferred stranded configuration of the present invention is particularly desirable because the novel design provides a high surface area to volume ratio to maximize interchange between the matrix and wound moisture and wound debris. The multiple strands of the preferred configuration provide maximal inter-strand space to serve as a reservoir for moisture, necrotic materials, or agents scheduled for delivery to the wound bed. The superior moisture absorption and regulation capacity of the preferred embodiment equip the wound dressing devices for use on heavily to moderately draining wounds.

In addition to increased moisture absorption and the ability to deliver active agents, the individual strands of the preferred configuration may participate in mechanical debridement thereby accelerating the wound healing process. The individual strands of the preferred wound dressings increase the inherent flexibility of the device, and enhance conformability to the irregularities of the contours in the wound cavity, allowing the preferred devices to be used in deeply cavitated wounds where debridement is essential. In order to simplify the overall wound dressing procedure, the preferred devices may have a single unit construction that is applied and removed as a complete unit, leaving no remnants. Additionally, the preferred devices may be left in place for prolonged periods between changes.

Accordingly, it is an object of the present invention to provide compositions and methods for the treatment of wounds.

Another object of the present invention is to provide compositions and methods that facilitate and accelerate the wound healing process.

Yet another object of the present invention is to provide a wound dressing device wherein active agents are incorporated.

It is another object of the present invention to provide wound dressing devices that absorb excess moisture at a wound site.

It is another object of the present invention to provide wound dressing devices that promote autolytic debridement.

Yet another object of the present invention is to provide a wound dressing device that absorbs wound exudate by allowing for optimal contact between the device and the wound area.

A further object of the present invention is to provide wound dressing devices for external and internal wounds.

Another object of the present invention is to prevent infection by providing wound dressing devices that clean wound sites by removing debris and contaminating material.

It is another object of the present invention to provide wound dressing devices that easily conform to the shape of a wound.

It is yet another object of the present invention to provide wound dressing devices that are easily manufactured.

Still another object of the present invention is to provide wound dressing devices that may be easily removed from wounds and replaced.

Yet another object of the present invention is to provide wound dressing devices that are compatible with injured tissue and do not induce irritation or inflammation.

It is yet another object of the present invention to provide wound dressing devices that function to both absorb wound exudate and promote autolytic debridement.

Another object of the present invention is to provide methods and compositions for making single unit construction wound dressing devices having multiple strands.

It is another object of the present invention to provide methods and compositions for treating wounds using wound dressing devices that function to both absorb wound exudate and deliver wound healing agents.

An object of the present invention to provide methods and compositions for treating wounds using wound dressing devices having active agents incorporated therein.

Still another object of the present invention is to provide methods and compositions for delivering active agents to wound sites and damaged tissue.

These and other objects, features and advantages of the present invention will become apparent after a review of the following detailed description of the disclosed embodiments and the appended claims.

BRIEF DESCRIPTION OF THE FIGURES

FIG. 1 is a three dimensional view of one embodiment of a wound dressing device of the present invention wherein the multi-stranded device may have free floating strand ends.

FIG. 2 presents a cross-section of a strand of the multi-strand device.

FIG. 3 is an illustration of a pattern of a die used for cutting a device from an appropriate matrix material.

DETAILED DESCRIPTION

Figure 4:
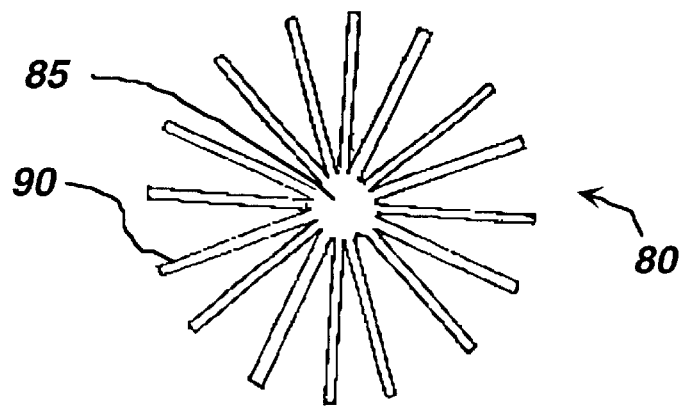
FIGS. 4–7 illustrate additional embodiments of a wound dressing device.

The present invention comprises compositions and methods for the treatment of wounds. In particular, the present invention comprises compositions and methods for treating wounds using wound dressing devices with active agents incorporated therein. In a preferred embodiment, the active agents may be directly incorporated into the matrix of the devices for controlled release at the site of the wound. In a further preferred embodiment, the matrix comprises a polymer network with a non-gellable polysaccharide dispersed evenly throughout said network. The matrices of this preferred embodiment provide a reliable and efficient means for delivering active agents to the wound while at the same time provide a superior moisture regulation capacity for promoting wound healing.

The wound dressing devices of the present invention may also take a particular conformation. For example, a preferred embodiment of the present invention comprises a stranded configuration wherein the individual strands extend from at least one common region and may have free floating ends. This particular conformation is particularly suitable for use in deeply cavitated wounds since the multiple matrix strands enable the dressing to conform to individual and uniquely shaped wound areas. Furthermore, the devices accelerate wound healing by displacing and allowing for the removal of excess cellular exudate and debris, thereby improving the rate of tissue repair and regeneration.

Definitions

The terms "a", "an" and "the" as used herein are defined to mean one or more and include the plural unless the context is inappropriate.

Active agents

The active agents incorporated into the wound dressing devices of the present invention may be used for the treatment of wounds or in skin healing. The active agents may participate in, and improve, the wound healing process, and may include antimicrobial agents, including but not limited to antifungal agents, antibacterial agents, anti-viral agents and antiparasitic agents, growth factors, angiogenic factors, anaesthetics, mucopolysaccharides, metals and other wound healing agents.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

Growth factor agents that may be incorporated into the wound dressing devices of the present invention include, but are not limited to, basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors α and β (TGF-α and TGF-β), interleukin-8 (IL-8); granulocyte-macrophage colony stimulating factor (GM-CSF); the interleukins, and the interferons.

Other agents that may be incorporated into the wound dressing devices of the present invention are acid mucopolysaccharides including, but are not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins that may be especially useful in the treatment of wounds include, but are not limited to, collagen, cross-linked collagen, fibronectin, laminin, elastin, and cross-linked elastin or combinations and fragments thereof. Adjuvants, or compositions that boost an immune response, may also be used in conjunction with the wound dressing devices of the present invention.

Other wound healing agents that are contemplated in the present invention include, but are not limited to, metals. Metals such as zinc and silver have long been known to provide excellent treatment for wounds. Delivery of such agents, by the methods and compositions of the present invention, provide a new dimension of care for wounds.

It is to be understood that in a preferred embodiment of the present invention, the active agents are incorporated into the wound dressing devices so that the agents are released directly from the devices and further delivered via transdermal or transmucosal pathways. The incorporated agents may be released over a period of time, and in this way, the devices retain their ability to kill or inhibit microorganisms or boost the body's immune response over an extended period of time in order to facilitate wound healing.

Administering active agents for the treatment of wounds by using the wound dressing itself overcomes several of the problems of the prior art. First, the present invention avoids the painful re-application of salves and ointments to the wound. The present invention also allows active agents to be delivered directly into the site of the wound to prevent the negative impact of system wide delivery of the agents as encountered after oral or intravenous administration. In the case of deeply cavitated wounds, in contrast to the topical application of active agents, the wound dressing and active agents therein may be located directly within the wound, providing a more effective delivery of the agents. Finally, in contrast to an injection of active agents, the present invention provides methods of administering active agents wherein the agents may be removed immediately from the wound and the administration terminated.

Matrices

The wound dressing devices of the present invention comprise a matrix material, and most preferably, having one or more active agents are incorporated therein. In a preferred embodiment of the present invention, the matrix is flexible and elastic, and is a semi-solid scaffold that is permeable to substances such as inorganic salts, aqueous fluids and dissolved gaseous agents including oxygen. The substances permeate the matrix through movement via intermolecular spaces among the cross-linked polymer.

Preferably, the matrix material is constructed from a natural or synthetic polymer and a non-gellable polysaccharide. Natural polymers that may be used for the construction of the wound device include, but are not limited to collagen, animal hide, hyaluronic acid, dextran and alginate. Synthetic polymers that may be used include, but are not limited to polyacrylamide, polyacrylate, polybuterate, polyurethane foam, silicone elastomer, rubber, nylon, vinyl or cross linked dextran. If cross-linked dextran is used, it is preferred that the molecular weight of the dextran polymer is between 50,000 and 500,000. The most preferable non-gellable polysaccharide is a non-gellable galactomannan macromolecule such a guar gum. A range of guar gum between approximately 0.01 kg to 100 kg, preferably between approximately 0.1 kg to 10 kg, and most preferably between approximately 0.5 kg to 2 kg is generally sufficient. Other non-gellable polysaccharides may include lucerne, fenugreek, honey locust bean gum, white clover bean gum and carob locust bean gum.

To decrease the permeability of wound dressing devices comprising a cross-linked polymer and non-gellable polysaccharide matrix, water loss control agents may be applied to the surface of the device. Application of water loss control agents is preferred since a decrease in the permeability of the device controls the loss of fluids from the wound. The preferred water loss control agent is petrolatum, however, other water loss control agents such as glycolipids, ceramides, free fatty acids, cholesterol, triglycerides, sterylesters, cholesteryl sulfate, linoleic ethyl ester and silicone oil may also be used.

If desired, a plasticizer may also be added to the matrix material. The presently preferred plasticizer is glycerol and water, however, propylene glycol and butanol may also be used. If glycerol is used, a range of between approximately 0.5 kg to 50 kg, preferably between 1 kg and 30 kg, and most preferably between approximately 5 kg to 15 kg is generally sufficient. The plasticizer may be added in the initial mixture of polymer and cross-linking agent.

If desired, a hydration control agent may be incorporated into the matrix. The preferred hydration control agent is an isopropyl alcohol, however, ethanol, glycerol, butanol, and propylene glycol may also be used. A range of isopropyl alcohol of between approximately 0.1 kg to 10 kg, preferably between approximately 0.2 kg to 5 kg and most preferably between approximately 0.5 kg to 2 kg is generally sufficient.

The matrix of the preferred embodiment preferably comprises polymerized chains of acrylamide monomer, wherein the acrylamide monomers are cross-linked with a cross-linking agent, a non-gellable polysaccharide, and an active agent or pharmaceutical directly encapsulated into microcavities therein. A range of acrylamide between approximately 1 kg to 100 kg, preferably between approximately 2 to 50 kg, and most preferably between approximately 5 kg to 20 kg is generally sufficient.

The most preferable cross-linking agent is NNNN'-methylenebisacrylamide, however other appropriate cross-linking agents such as bisacrylylycystamine and diallyltartar diamide may also be used. If NNNN'-methylenebisacrylamide is used, a range of between approximately 0.01 kg to 1 kg, preferably between approximately 0.02 kg to 0.5 kg, and most preferably between approximately 0.05 kg to 0.3 kg is generally sufficient. As noted above, the most preferable non-gellable polysaccharide is a non-gellable galactomannan macromolecule such a guar gum, but other non-gellable polysaccharides may include lucerne, fenugreek, honey locust bean gum, white clover bean gum and carob locust bean gum.

Ammonium persulfate and TEMED may also be added to the matrix. A range of ammonium persulfate between approximately 0.01 kg to 1 kg, preferably between approximately 0.02 kg to 0.5 kg, and most preferably between approximately 0.05 kg to 0.2 kg is generally sufficient. Additionally, a range of TEMED between approximately 0.01 kg to 1 kg, preferably between approximately 0.02 kg and 0.5 kg, and most preferably between approximately 0.05 kg to 0.3 kg is generally sufficient.

Incorporation of active agents

One embodiment of the matrices of the present invention can be found in U.S. Pat. No. 5,196,190 to Nangia et al., which is hereby incorporated in its entirety. Nangia et al. teach a matrix composed of a natural or synthetic polymer, a non-gellable polysaccharide, and a phospholipid based drug delivery system. In particular, Nangia et al. teach a matrix capable of drug delivery, wherein lipid vesicle liposomes containing a desired drug are incorporated into the matrix.

One problem with the prior art methods, however, is the difficulty of incorporating active agents into the liposomes since some agents may be incompatible with liposome chemistry. Incorporation using liposomes is time consuming, expensive and sometimes unreliable because dispersion of the liposomes in the matrix is difficult to achieve and once achieved, the liposomes may prematurely release costly agents due the liposomes' inherent instability. Another problem is that the prior art fails to teach a method of incorporating active agents into a wound dressing wherein the release of the agent over time can be controlled through the manipulation of concentration parameters, movement of water through the matrix and the degree of cross linking in the matrix.

Preferred embodiments of the present invention however, address the need for a less expensive, quicker, and more reliable method for incorporating a wider range of desired agents into wound dressing devices. Preferred embodiments also provide a means to control the release of the desired agents over time via manipulation of concentration parameters, movement of water through the matrix and the degree of cross-linking in the matrix. In a preferred embodiment, the desired agents may be directly incorporated into the matrix by adding the agents into the initial formulation for the matrix prior to cross-linking. This method of incorporation is inexpensive, rapid and reliable, and most surprisingly, the incorporated agents are not affected by the process of polymerization and retain their biological activities.

Using preferred embodiments of the present invention, delivery of the desired agents may be controlled by the use of movement of liquid through the matrix. Though not wishing to be bound by any theory, it is theorized that the liquid in a matrix of polymer and non-gellable polysaccharide is either bound to the non-gellable polysaccharide or it is unbound in the polymer mass. Thus, it is theorized that the present invention uses the free liquid portion of the matrix as a general solvent and as a means to deliver desired agents. Soluble drugs are easily dissolved in the free liquid portion, however slightly soluble drugs are ground to a fine powder and may require the use of a wetting agent such as glycerol or isopropyl alcohol or a surfactant such as polysorbate, triton-X or sodium lauryl sulfate.

Once the desired active agent or agents are dispersed throughout the matrix, a portion of the agent resides in the non-gellable polysaccharide, while another portion of the agent is dissolved in the free liquid phase and moves freely through the matrix. The ability of the agent to move freely throughout the matrix in the free liquid phase is important in the agent delivery system of the present invention. Because the agent is dissolved in the free liquid phase, a concentration gradient of the active agent is created between the matrix of a wound dressing device and the moisture of the wound itself. Therefore, when the matrix is placed onto a moist surface such as an open wound, the soluble agent will move through the free liquid phase toward the agent-free wound moisture, resulting in the delivery of the agent to the wound. This movement of soluble agent further upsets the equilibrium between soluble and insoluble agents, and causes more agent to dissolve into the free liquid phase, thus causing more agent to be delivered to the wound. Because the present invention incorporates the desired agent directly into the matrix rather than incorporating the drug into other delivery vehicles, such as liposomes, the agent may be dissolved in the free liquid phase and reliably delivered to the wound through the process described above.

Delivery of the desired agents may also be controlled by the degree of cross-linking in the matrix. As described above, the desired agents may be added to the other ingredients forming the matrix prior to the addition of the cross-linking agent. Subsequent addition of the cross linking agent and concomitant polymerization results in both chain elongation of monomeric chemicals and cross-linking between chains of monomers. The combination of chains cross-linked together creates micro-cavities wherein the desired agents are encapsulated. By controlling the amount of cross-linking agent and the length of chains of monomer, it is possible to regulate the size of the micro-cavities in the polymer. Larger micro-cavities, produced by a lower degree of cross-linking, allow for freer migration and quicker delivery of the desired agent, whereas smaller micro-cavities increase the delivery time. Although the liposome based delivery system may also make use of the degree of cross-linking, the liposome itself acts as an additional barrier to delivery, making delivery less controlled and less reliable.

Stranded structure

The wound dressing devices of the present invention may take many physical forms, however, preferred embodiments are primarily constructed of thin strands of matrix suitable for placement into the wound bed or cavity. The preferred devices may be constructed from one or multiple strands of matrix. When multiple strands are used in the construction, the strands are secured together by wrap, tie, glue, or alternatively by a continuous bridge of matrix between adjacent strands. Multiple strands are secured together to minimize accidental loss during removal of the dressing from the wound bed. Typically, the strands of particular embodiments are bound or secured in the mid-region so that the ends of the device may float free. The advantage of free floating strands is to enable the individual strands to access a maximum volume of the wound and thereby absorb the excess fluid, exudate and debris. The mechanical action of the free floating strands contributes to the trapping and removal of cellular and wound debris. Concurrently the free floating strands also conform optimally with the contours of the wound surface to maximize contact between the device and the wound bed.

Referring now to the drawings, one preferred conformation of the wound dressing devices of the present invention is now described. This preferred conformation is useful for the control of exudate moisture accumulation, for stimulation of mechanical and autolytic debridement, and for delivery of active agents.

FIG. 1 is a three dimensional view of a preferred embodiment of the wound dressing device 10 with a strand 20 of the multi-strand device with free floating strand ends 40. The strands are secured together by a bridge 30 created during the cutting stage and composed of the matrix material used to construct the device. FIG. 2 represents a cross-section 22 of a strand 20 of the multi-strand device 10. It is intended that the cross-section 22 illustrate the sum of the linear dimensions of the sides. Preferably the sum of the linear dimensions of the sides is at least twice the numerical value of the surface area of the cross-section to provide an adequate surface area to volume ratio of the strands. More preferably, the sum of the linear dimensions of the sides is four or more times the numerical value of the surface area of the cross section.

FIG. 3 is an illustration of the pattern of a die 45 used for cutting a preferred embodiment of the wound dressing device 10 from an appropriate matrix material. Cutting blades 55, around the perimeter of the die, release the cut-out from the stock sheet of matrix during the cutting phase of production. Within the perimeter, a series of cutting blades 57 are situated lying parallel to one another extending from the ends of the pattern toward the center but not continuing through the center so as to leave a region 50 of uncut material in the center. The pattern of blades may vary according to the purpose of the wound dressing device. For example, the patterns may vary in terms of numbers of strands 20, numbers of regions of uncut region 50 for bridging strands, and the positioning of the single or multiple bridges 50 relative to the ends of the strands. The cross section 22 of the strands may be any suitable dimension that allows the appropriate interaction between strands and wound environment. The matrix may be any non-dissolving material that is suitable for contacting the broken skin, and underlying tissues including non-absorbent natural or synthetic materials, or absorbent natural or synthetic materials.

Figure 5:
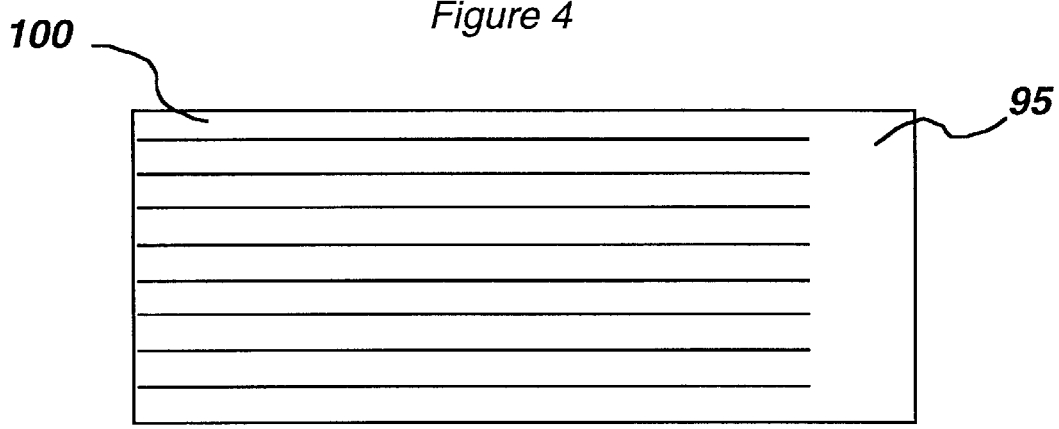
Figure 6:
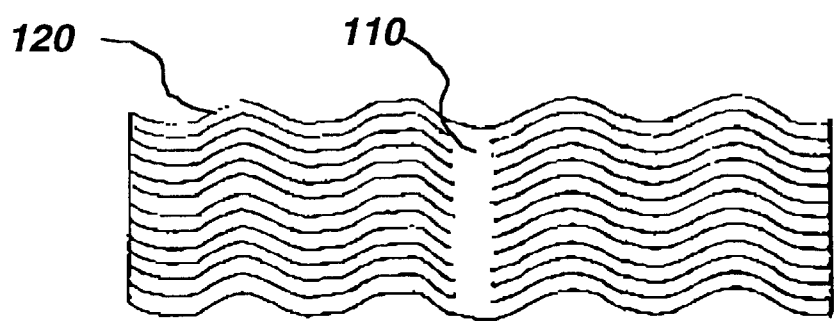
Figure 7:
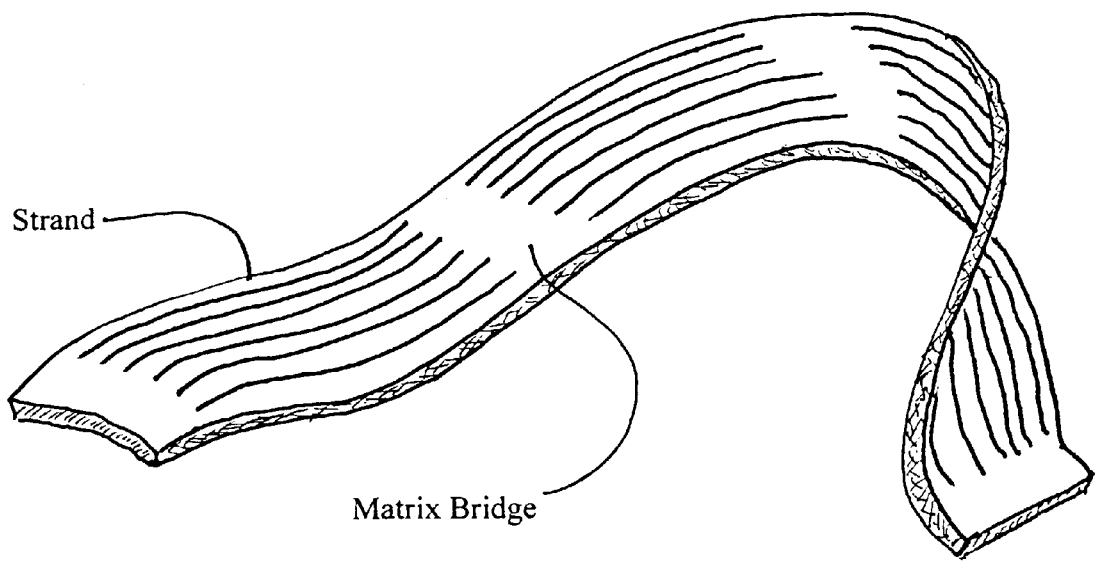

FIG. 4 illustrates a pattern that is an alternative embodiment. It is a circular pattern for making an embodiment 80 whereby the strands 90 radiate away from a central region of uncut matrix that joins the adjacent strands in the unit. FIG. 5 illustrates a pattern for making an embodiment whereby the bridge 95 of matrix is offset to one end of the pattern enabling the strands 100 to radiate away from the bridge in a single direction. FIG. 6 illustrates a pattern for making an embodiment whereby the strands 120 are irregular in shape over their length from the matrix bridge 100. FIG. 7 illustrates a pattern for making an embodiment whereby the strands are conjoined at several bridges along the length of the device and at the ends of the device. It is to be understood that the pattern can be any variation of these embodiments and is still within the scope of the present invention.

The unique stranded embodiment is particularly desirable because it enables the device to maintain its integrity and also maximize the surface area to volume ratio of its matrix. This is important since the matrix may be an absorbent material where a high surface area to volume ratio increases the rate of absorption, without increasing the overall absorption capacity of the device.

In a preferred embodiment, the wound dressing is principally constructed of a "stranded" matrix, which allows for optimal contact between the strands and the wound area. In addition, the stranded matrix construction maximizes the overall flexibility and pliability of the dressing. In embodiments of the device where multiple strands are employed, the overall flexibility and conformational characteristics of the device are maintained by binding strands in only limited and restricted areas. Minimal binding of the strands prevents the formation of rigid areas and allows for the effective and optimal utilization of numerous strands in a single device without adversely diminishing contact with the surface of the wound bed.

Another advantage of the stranded matrix construction is the "semi-porous" quality of the wound dressing that allows for the removal of extraneous cellular matter resulting during the wound healing process. The air in the inter-strands area of the device serve as a reservoir of space that may be displaced allowing for the removal of excess materials such as exudate fluid, debridement product and cellular exudate from the wound bed. As this region fills, the device may swell to provide "support" to the wound bed and surrounding tissues. A wound constitutes damaged or "missing" tissue, and when tissue is missing, the surrounding tissue may "collapse" or sag into the void. "Support" in this context therefore, means the temporary filling of the void to hold the surrounding tissue in place where it should reside.

Removal of debridement product and cellular exudate is further facilitated by unbound, loose strands of the wound dressing devices. When placed upon a wound, the loose strands of the devices randomly orient in the wound bed where the thin filamentous strands and free floating ends contribute to mechanical debridement of necrotic slough. Since the strands are secured and bound in at least one region, a mechanical union is formed, ensuring that all strands and necrotic tissue accumulation in the inter-strand spaces are removed from the wound when the device is changed. By contributing to the removal of extraneous wound products and cellular debris, the wound dressing device permits cleaning of the wound which in turn prevents and decreases the possibility of infection and contamination.

In one embodiment, the wound dressing device is constructed from a matrix composed of an absorbent synthetic polyacrylate material. The rate of absorption of polyacrylate is significantly increased by cutting the material into strands, which increases the surface area to volume ratio. Polyacrylate material is particularly suitable for the wound dressings of the present invention because it retains its integrity during interaction with wound exudate moisture, as well as with necrotic tissue and wound debris. The wound dressing device of the present invention does not dissolve, gel or otherwise disintegrate during application to the wound. The preferred matrix swells slightly during the absorption of moisture, causing the device to conform closely to the walls of the wound bed.

In a preferred embodiment, the polyacrylate matrix is cut into free-floating strands bound together through a matrix-bridge in the mid-region. This pattern of construction imparts a significantly high surface area to volume ratio for rapid moisture movement within the absorbent matrix.

Wound dressing devices of the present invention may be produced by cutting a desired design pattern from stock sheets of matrix material. For example, the material may be die-cut from stock sheets of an absorbent polyacrylate wound dressing material. The stranded cut-out may then be coated with an agent to prevent aggregation and tangling of the free floating strands. Coating agents that may be used include, but are not limited to, petrolatum, talcum, polyglycols, glycerol, propylene, glycol, vegetable oil, and animal oil. Following the steps of cutting and coating, the material may be sterilized using sterilization techniques known in the art such as gamma radiation, steam and heat sterilization, electron beam or chemical sterilization (such as by use of ethylene oxide).

A preferred composition of the present invention comprises a matrix comprising a polymer, a non-gellable polysaccharide, and one or more active agents incorporated therein. A more preferred matrix comprises an acrylamide polymer, guar gum, and one or more active agents incorporated therein. A most preferred matrix comprises an acrylamide polymer, guar gum, has one or more active agents incorporated therein, and is formed into a stranded structure wherein the strands are secured by at least one common region.

The wound dressing devices of the present invention may be used on injured tissue and for bodily fluid drainages where control and management of fluid and secretions is desired. The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions.

In particular, the wound dressing devices of the preferred embodiments are especially applicable for usage on heavily exudating acute and chronic wounds for controlling accumulating exudate moisture, support of the wound bed and surrounding tissues. Importantly, the wound dressings are particularly effective for stimulating and supporting autolytic debridement, and therefore accelerating the wound healing process.

In use, the wound dressing devices of the present invention are the primary dressing placed in direct contact with the wound bed, or as near as practical against the wound bed. The devices may serve as a packing material and, if required, may be secured into position with any suitable secondary wound dressing such as a wrap, tape, gauze, or pad. The dressings are temporary, however, and are not intended for permanent incorporation into the healed tissues. When necessary, the wound dressing devices are changed by first removing any over-dressing material and then removing the device, whereby any accumulated necrotic tissue and exudate is lifted away. The wound dressing devices of the present invention may be replaced by a fresh device or other suitable wound covering.

The devices may be placed in their entirety into a wound, placed in combination with additional bundles of the same design into the wound, or cut through the bridge between strands to reduce the size or number of strands present in the wound.

The devices of the present invention may be cut, shaped and modified to accommodate numerous uses and applications. For example, the devices may be used as a gastric retrievable device, wherein a retrieval cord is attached to the device that is then swallowed. After absorption has taken place, the devices may be retrieved and analyzed for content.

The devices may undergo a swelling action as they absorbs exudate moisture, however, they will not dissolve or disintegrate. The swelling action displaces necrotic material from the wound surface and forces the material into the inter-strands regions of the device. The laden moisture content and the retention of moisture near the wound bed by the invention contributes to stimulation of the autolytic debridement process whereby the body's own enzymes break-up necrotic tissue and cellular debris. Complete removal of the device occurs due to the conjoined nature of the device.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Formation of a Matrix Including Acrylamide

A mixing tank was charged with 161.4 kg of water and 9.1894 kg of acrylamide, 0.10347 kg of NNNN'-methylenebisacrylamide, and 9.3046 kg of glycerol were added and mixed. Then 1.0213 kg of guar gum non-gellable polysaccharide was dispersed in a mixture containing 0.9770 kg of isopropyl alcohol and 2 kg of water. The solution of guar gum was then added and dispersed into the acrylamide mixture. After suitable mixing, 0.1042 kg of TEMED was added and polymerization was catalyzed with 0.0999 kg ammonium persulphate.

While the batch was still liquid, it was poured into molds to form sheets. After gelling had occurred, sheets were transferred to a dessicator and dehydrated to form a stable intermediate stock sheet. Prior to cutting to size, the stock material was re-hydrated in a humid atmosphere. After cutting, the material was coated with petrolatum. The resulting wound dressing device was then sealed into appropriate packaging and irradiated to sterilize it.

EXAMPLE 2

Absorption Capacity of Polyacrylamide Matrix

It was determined that a preferred matrix material composed of cross-linked polyacrylamide and embedded natural vegetable gum absorbed approximately seven times its weight in water. Saturation of a flat sheet of matrix material with a thickness of 0.9 mm was achieved in approximately 22 hours of continuous exposure to excess water. A similarly sized piece of flat matrix material was cut into thin strands with a calculated 200% increase in overall surface area. The total water absorption of this material was also approximately seven times its weight. However this material achieved saturation in approximately five hours. Similar comparisons were made between an intact matrix and a matrix cut in such a way as to increase the surface area between 150% and 300%. These studies revealed that the matrices retained their overall absorption capacity but there was an increased rate of absorption proportional to the increase in surface area.

EXAMPLE 3

Matrix Absorption Capacities for Various Natural Substances

Matrices, cut into strands, were tested for absorption capacities on a variety of natural aqueous based viscous fluids. These fluids included water containing salt (0.15M salinity), cow's whole milk, egg whites from chicken eggs, yogurt, and fetal bovine serum. The absorption of moisture by the test matrix strands ranged between 3.2 and 7.3 times the original weight of the tested devices.

EXAMPLE 4

Absorption Capacity of Matrix in Heterogeneous Biological Fluid

A polyacrylamide matrix of a preferred device was placed into a test tube containing fetal bovine serum, in an amount equal to five times the weight of the matrix. The matrix absorbed the aqueous fluid from the serum, leaving a concentrate of serum proteins in approximately four hours at 4° C. The concentrated serum proteins were predominately located between the strands of the device as a thick viscous coagulation. When the device was removed from the tube, the concentrated proteins were also removed. This experiment showed that the design would assist in the debridement of the wound.

EXAMPLE 5

Construction of Stranded Matrices

Initial prototypes of the stranded matrices were prepared by taking flat sheets of polyacrylamide matrix and cutting them into thin strands using a sharp instrument such as a box knife. Several methods were tested to determine a satisfactory method for commercial production of the device. The following tests were carried out with success:

Test 5(a). Matrix material was processed through a pasta cutter using a blade for noodles.

Test 5(b). A steel rule die was constructed such that parallel bands of steel rules, separated by spacers were locked into a die block. Matrix was cut by placing the die over the matrix and press-cutting with a hydraulic press.

Test 5(c). Matrix formula was compounded and catalyzed to initiate polymerization. The matrix was then placed into a 50 ml syringe and extruded as a thin strand onto a sheet. The thin strands were allowed to complete polymerization and then were dried and cut to uniform lengths for use in the device.

Test 5(d). A rotary die was constructed with a preferred pattern. The rotary die was placed into the rotary die assembly and matrix was fed through between the rotary die and the anvil for cutting.

EXAMPLE 6

Optimization of Matrix Construction Utility

Several prototypes were constructed to optimize the utility of the device as follows:

Test 6(a) Individual strands cut from a sheet of matrix were banded together using a silicone elastimer ring. The ring, having an internal diameter of approximately 3 mm and a length of 1.5 mm, was stretched open so that between five to seven strands could be threaded through and secured by the band about the middle. When placed into fluid for absorption studies, it was found that the unit nature of the device was retained throughout the absorption period and that the whole device was removed without leaving remnants in the absorption chamber.

Test 6(b) Prototypes constructed by using one strand to tie other strands together performed satisfactorily in absorption and retrieval studies.

Test 6(c) Prototypes constructed by maintaining a continuous bridge of matrix between adjacent strands were tested and shown to perform satisfactorily in absorption and retrieval studies.

EXAMPLE 7

Incorporation of Penicillin G into the Matrix

The incorporation of the antimicrobial agent, penicillin G, into the matrix was evaluated by dissolving $1\times10^6$ units of penicillin G powder into 50 milliliters of water. Acrylamide, methylenebisacrylamide, glycerol, and a guar gum/isopropyl alcohol mixture were added to a flask containing 900 ml water and mixed for two hours. The penicillin solution was then added to the flask along with TEMED dissolved in 25 ml water. After thorough mixing, ammonium persulphate in 25 ml water was added and mixed thoroughly. The mixture was then poured into sheet molds and allowed to gel. The sheets of semi-solid gel material were stripped from the mold and dehydrated to approximately 7% their original water content for storage. Prior to testing, the sheets were placed in a humidified environment until the sheet weight had increased to approximately 118–122% the storage weight. Discs of 0.7 cm diameter were cut from the sheets. The discs were placed onto the surfaces of agar plates that had previously been seeded with various strains of microorganisms (*Staph aureus; E. coli; Candida albicans; Ps aeruginosa*). The plates were incubated and then examined for zones of inhibition around the discs containing antibiotic verses control discs. Zones of inhibition were measured around the penicillin containing matrix but not the control matrix on the *Staph aureas, E coli,* and *Pseudomonas aeruginosa* plates. No zone was measured on the *Candida albicans* plate. These results demonstrate the release of active penicillin G after its incorporation into the matrix.

EXAMPLE 8

Incorporation of Silver Chloride Precipitate into the Matrix

Silver chloride is a weakly soluble salt that dissociates in water to release the silver ion that may have antimicrobial activity. Silver nitrate was dissolved into the batch mixture of pre-polymerized matrix at a concentration of $5\times10^{-3}$M and then mixed well. The silver was precipitated by the addition of sodium chloride to produce a colloidal suspension of the weakly soluble salt. The batch was then polymerized by the addition of TEMED and ammonium persulphate and cast into sheets. The sheets were dehydrated to approximately 5% of the original moisture content and stored in the dark. Before testing, the sheet stock was hydrated to 118–122% its storage weight and then cut into 0.7 cm discs that were placed on the surface of pre-inoculated agar culture plates. The plates were incubated and then evaluated for growth around the discs.

Zones of inhibition were measured around discs on plates inoculated with *Staph aureus; E. coli; Candida albicans; Pseudomonas aeruginosa,* indicating the release of active silver ions after incorporation into the matrix. Hydrated sheets exposed to continuous light turned from an amber color to a uniform tan to brown color which illustrated uniform dispersion of the silver chloride precipitate.

EXAMPLE 9

Synergistic Action Between Therapeutic Agent and Adjuvant

The antifungal agent Zn-pyrithione is an active agent against a wide range of pathogenic fungi but it poorly penetrates heavily keratinized tissues such as finger and toe nails. Matrix material containing Zn-pyrithione and the keratinolytic agents salicylic acid and urea were tested for increased efficacy of delivering agents to control fungal growth in nail tissue. To the pre-polymerized batch material was added sufficient Zn-pyrithione, salicylic acid and urea to give final concentrations of 0.01%, 5% and 5%, respectively. The batch was neutralized to pH 6.5 by the addition of sodium hydroxide. After thorough mixing, the batch was poured into molds to cast into sheets. After gelling, the sheets were dehydrated to 5% the original moisture content and stored. Before testing, the sheet stock was hydrated to 118–122% its storage weight and then cut into 0.7 cm discs which were placed on the surface of bovine hoof material cut thinly to resemble finger nail. These were then transferred onto pre-inoculated agar culture plates. The plates were incubated and evaluated for growth around the discs.

Zones of inhibition were measured around the discs on plates inoculated with Candida albicans. No zones were measured where Zn-pyrithione or the keratinolytic agents were not included in the matrix. Smaller zones were measured where only urea and Zn-pyrithione were added. Zones of inhibition were however measured around sets that contained both the active agent and the keratinolytic agents in combination. These results demonstrate that therapeutic agents and adjuvants may be incorporated into the matrix and later released in active form such that they work synergistically.

EXAMPLE 10

Bovine Protein Incorporation into and Delivery from the Matrix

Bovine serum albumin (approximately 65,000 Daltons) and bovine gamma globulin (approximately 155,000 Daltons) were dissolved at a concentration of 0.1% w/w into a pre-polymerized matrix batch material and thoroughly mixed. The batch was polymerized by the addition of TEMED and ammonium persulphate, poured into molds and gelled into sheets. The sheets were dehydrated to approximately 5% the original moisture content and stored. Before testing, the sheet stock was hydrated to 118–122% its storage weight and then cut into 0.7 cm discs which were placed on the surface of saline agar plates. The plates were incubated for 24 hours at 4° C. and then developed by the addition of 0.25M HCl solution which causes proteins to precipitate. Zones of protein precipitate were measured only around the discs that had protein incorporated into the matrix, indicating the release of active protein after its incorporation into the matrix.

EXAMPLE 11

Interleukin-2 Incorporation into and Delivery from the Matrix

The growth factor interleukin-2 was incorporated into polymerized matrix material by soaking re-hydrated plain stock sheet in fluid containing the growth factor. After 24 hours of soaking at 4° C., the matrix pieces were cut into one cm circles and placed into saline. Samples of the elution fluid were taken at intervals and assayed by ELISA (Enzyme Linked Immunosorbent Assay) for interleukin-2 to determine if material entered the matrix and was then released. The results showed that proportionately more IL-2 was eluted from the matrix over time.

EXAMPLE 12

Temporal Release of Antifungal Agent

Fluconazole was incorporated by the addition of the active agent to a pre-polymerized batch of matrix. After polymerization, dehydration and rehydration, a disc containing the active agent was placed onto an agar plate for two hours at 4° C. Thereafter, every two hours for a total of 154 hours, the disc was removed and transferred to a new spot on the surface of the agar. After all transfers had been carried out, the plates were inoculated with Candida albicans and incubated at 35° C. until confluent growth had occurred. The serial transfer spots on the plates were then examined for zones of inhibition. The results showed that the device delivered a high dose of fluconazole in the first eight hours and then a steady concentration thereafter until the 140th hour when the concentration, according to zone size, began to diminish.

EXAMPLE 13

Delivery of a Biologically Functional Protein from the Matrix

Human transferrin is an iron chelating protein of approximately 70,000 MW. Transferrin was incorporated into the pre-polymerized batch mix at 0.05% w/w, mixed, and then encapsulated by polymerization with TEMED and ammonium persulphate. After dehydration, rehydration and cutting, discs of 0.7 cm were placed onto the surface of nutrient agar plates and incubated at 4° C. for 24 hours. The discs were then removed and the plates were inoculated with Staph aureus and then incubated at 37° C. overnight. The plates were examined for zones of inhibition where the transferrin removed the trace element iron from the nutrient. Human transferrin retained its biological activity during incorporation, processing and testing as measured by the zones of inhibition around the spots where transferrin-containing discs had been placed.

It should be understood that the foregoing relates only to preferred embodiments of the present invention and that numerous modifications or alterations may be made therein without departing from the spirit and the scope of the invention as set forth in the appended claims.

What is claimed is:

1. A wound dressing device, comprising a biocompatible matrix comprising a polymer network and a non-gellable polysaccharide, wherein the matrix is configured into multiple strands; wherein a portion of each strand is secured at a common region; and wherein at least one end of each strand is free floating, and having one or more active agents directly incorporated therein.

2. The device of claim 1, wherein the non-gellable polysaccharide is a non-gellable galactomannan selected from the group consisting of guar gum, honey locust bean gum, white clover bean gum, and carob locust bean gum.

3. The device of claim 1, wherein the non-gellable galactomannan is guar gum.

4. The device of claim 1, wherein the polymer is polyacrylamide.

5. The device of claim 1 further comprising a water loss control agent, a plasticizer, and a hydration control agent.

6. The device of claim 1, wherein the active agents comprise a therapeutic agent and an adjuvant.

7. The device of claim 1, wherein the active agent is selected from the group consisting of antimicrobial agents, antifungal agents, antiviral agents, metals and wound healing agents.

8. The device of claim 7, wherein the active agent is an antimicrobial agent selected from the group consisting of isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, zinc pyrithione, and silver salts such as chloride, bromide, iodide and periodate.

9. The device of claim 7, wherein the wound healing agents are selected from the group consisting of growth factors, mucopolysaccharides and proteins.

10. The device of claim 9, wherein the growth factor is selected from the group consisting of fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors $\alpha$ and $\beta$ (TGF-$\alpha$ and TGF-$\beta$), interleukin-8 (IL-8); granulocyte-macrophage colony stimulating factor (GM-CSF); the interleukins, and the interferons.

11. A method for treating wounds, comprising administering a wound healing device comprising a biocompatible matrix comprising a polymer network and a non-gellable polysaccharide wherein the matrix is configured into multiple strands: wherein a portion of each strand is secured at a common region; and wherein at least one end of each strand is free floating, and having one or more active agents directly incorporated therein.

12. The method of claim 11, wherein the active agent is selected from the group consisting of antimicrobial agents, antifungal agents, antiviral agents, metals and wound healing agents.

13. The method of claim 11, wherein the active agent is selected from the group consisting of antimicrobial agents, antifungal agents, antiviral agents, metals and wound healing agents.

14. The method of claim 13, wherein the active agent is an antimicrobial agent selected from the group consisting of isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, zinc pyrithione, and silver salts such as chloride, bromide, iodide and periodate.

15. The method of claim 13, wherein the wound healing agents are selected from the group consisting of growth factors, mucopolysaccharides and proteins.

16. The method of claim 13, wherein the growth factor is selected from the group consisting of fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors $\alpha$ and $\beta$ (TGF-$\alpha$ and TGF-$\beta$), interleukin-8 (IL-8); granulocyte-macrophage colony stimulating factor (GM-CSF); the interleukins, and the interferons.

\* \* \* \* \*